United States Patent
St Amant, III

(10) Patent No.: US 10,222,302 B1
(45) Date of Patent: Mar. 5, 2019

(54) CYCLONIC SYSTEM FOR ENHANCED SEPARATION IN FLUID SAMPLE PROBES AND THE LIKE

(71) Applicant: Mayeaux Holding LLC, Gonzales, LA (US)

(72) Inventor: Valmond Joseph St Amant, III, St Amant, LA (US)

(73) Assignee: Mayeaux Holding LLC, Gonzales, LA (US)

( * ) Notice: Subject to any disclaimer, the term of this patent is extended or adjusted under 35 U.S.C. 154(b) by 345 days.

(21) Appl. No.: 14/924,469

(22) Filed: Oct. 27, 2015

Related U.S. Application Data

(60) Provisional application No. 62/076,472, filed on Nov. 6, 2014.

(51) Int. Cl.
*B01D 45/16* (2006.01)
*G01N 1/20* (2006.01)
*B04C 3/06* (2006.01)

(52) U.S. Cl.
CPC ........... *G01N 1/2035* (2013.01); *B01D 45/16* (2013.01); *B04C 3/06* (2013.01)

(58) Field of Classification Search
CPC ..... G01N 2001/2267; G01N 2001/227; G01N 1/22–1/24; G01N 1/2202–1/2211; G01N 2001/225; G01N 1/2247; G01N 2001/2285; G01N 1/2288; B01D 35/0276; B01D 36/008; B01D 45/12; B01D 45/16; B04C 3/00; B04C 2009/008; B04C 11/00
See application file for complete search history.

(56) References Cited

U.S. PATENT DOCUMENTS

| | | | | |
|---|---|---|---|---|
| 3,014,553 | A | * 12/1961 | Jerman | B01D 45/12 55/349 |
| 3,471,775 | A | 10/1969 | Birnstingl | |
| 3,581,467 | A | * 6/1971 | Donnelly | B01D 47/021 126/299 E |
| 3,778,977 | A | * 12/1973 | Conn | B01D 50/00 55/325 |
| 3,831,452 | A | * 8/1974 | Pittenger | G01N 1/22 73/863.82 |
| 4,481,833 | A | 11/1984 | Bajek | |
| 4,497,714 | A | * 2/1985 | Harris | B01D 17/0208 210/114 |

(Continued)

OTHER PUBLICATIONS

Collins Products Co, Collins Products Company Catalog, Jan. 2008, 60 pages.*

(Continued)

*Primary Examiner* — Peter J Macchiarolo
*Assistant Examiner* — Alexander A Mercado
(74) *Attorney, Agent, or Firm* — Joseph T Regard Ltd plc

(57) ABSTRACT

A cyclonic filter separator system, as well as alternatives, suitable for use as liquid block apparatus integrated into a sample probe that is inserted into the pressurized process to prevent entrained liquids from entering the probe and being extracted for sampling is provided. The present invention enhances sampling of pressurized process fluids for on-stream and spot sampling of pressurized process fluid such as natural gas or the like, particularly pressurized process gas having liquid entrained therein, or otherwise referenced as multiphase or "wet".

39 Claims, 13 Drawing Sheets

(56) References Cited

U.S. PATENT DOCUMENTS

| | | | |
|---|---|---|---|
| 4,586,390 A * | 5/1986 | Helke | G01N 1/2247 73/863.58 |
| 4,624,779 A * | 11/1986 | Hurner | B01D 17/0208 210/180 |
| 4,838,906 A * | 6/1989 | Kiselev | B01D 1/305 261/79.2 |
| 5,237,881 A | 8/1993 | Ross | |
| 5,579,803 A * | 12/1996 | Welker | F16K 24/046 137/202 |
| 5,698,014 A * | 12/1997 | Cadle | B01D 19/0063 166/357 |
| 5,755,965 A * | 5/1998 | Reiber | B01D 19/0057 210/512.1 |
| 5,777,241 A * | 7/1998 | Evenson | G01N 1/2258 73/863.11 |
| 6,003,362 A * | 12/1999 | Dieckmann | G01N 21/552 356/43 |
| 6,210,575 B1 | 4/2001 | Chase et al. | |
| 6,284,547 B1 * | 9/2001 | Schafer | G01N 1/2247 436/173 |
| 6,332,356 B1 * | 12/2001 | Hecht | G01F 1/6842 73/114.34 |
| 6,357,304 B1 * | 3/2002 | Mayeaux | G01N 1/2035 73/863.12 |
| 6,701,794 B2 | 3/2004 | Mayeaux | |
| 6,764,536 B2 * | 7/2004 | Welker | G01N 1/2247 55/417 |
| 6,818,045 B2 | 11/2004 | Welker | |
| 6,851,309 B2 * | 2/2005 | Lenzing | F02M 35/021 73/204.22 |
| 6,904,816 B2 | 6/2005 | Mayeaux | |
| 7,004,041 B2 | 2/2006 | Mayeaux | |
| 7,097,693 B1 * | 8/2006 | Mayeaux | B01D 29/56 210/188 |
| 7,134,318 B2 | 11/2006 | Mayeaux | |
| 7,337,683 B2 | 3/2008 | DeFriez et al. | |
| 7,907,693 B2 | 3/2011 | Bae et al. | |
| 8,087,308 B2 | 1/2012 | Gauthier et al. | |
| 8,176,766 B1 * | 5/2012 | Ruiz | G01N 1/2211 422/84 |
| 8,904,886 B1 * | 12/2014 | Mayeaux | G01N 1/2247 73/864.51 |
| 9,410,871 B1 * | 8/2016 | St Amant, III | G01N 1/2247 |
| 9,766,163 B2 * | 9/2017 | Knight | G01N 1/2247 |
| 2001/0015093 A1 * | 8/2001 | Kempe | G01N 1/2035 73/53.01 |
| 2002/0036167 A1 * | 3/2002 | Mayeaux | G01N 1/2035 210/637 |
| 2005/0223829 A1 * | 10/2005 | Mayeaux | G01N 1/2035 73/866.5 |
| 2007/0068223 A1 * | 3/2007 | Chen | G01N 1/2211 73/30.01 |
| 2007/0128079 A1 * | 6/2007 | Counts | G01N 1/04 422/400 |
| 2008/0307901 A1 * | 12/2008 | Knight | G01N 1/2247 73/863.11 |
| 2009/0107532 A1 * | 4/2009 | Lonne | B08B 9/00 134/56 R |
| 2011/0185892 A1 * | 8/2011 | Smith | G01N 1/2247 95/16 |
| 2011/0308311 A1 * | 12/2011 | Dalla Betta | G01F 1/6842 73/170.12 |
| 2012/0000366 A1 * | 1/2012 | Nixdorff | B01D 45/12 96/239 |
| 2014/0076027 A1 * | 3/2014 | Nicholson | G01N 1/2247 73/29.02 |
| 2015/0377750 A1 * | 12/2015 | Scipolo | G01N 1/2205 73/29.01 |
| 2017/0102298 A1 * | 4/2017 | Knight | G01N 1/2247 |

OTHER PUBLICATIONS

Dekati LTD of Finland, Dekati Cyclone product brochure, Aug. 2014, origin unknown.
Author Unknown, Cyclonic Separation, Wikipedia, Oct. 15, 2014, https://en.wikipedia.org/wiki/Cyclonic_separation.
Collins Products Co, Collins Products Company website image, 2014, www.collins-products.com.
A+ Corp, Tornado 602 Brochure, 2012.

* cited by examiner

CYCLONIC SYSTEM FOR ENHANCED SEPARATION IN FLUID SAMPLE PROBES AND THE LIKE

BENEFIT CLAIM

The present invention claims the benefit of U.S. Provisional Patent Application Ser. No. 62/076,472 filed Nov. 6, 2014, entitled "Cyclonic System for Enhanced Separation in Fluid Sample Probes and the Like", listing Valmond Joseph St Amant, III as inventor.

FIELD OF THE INVENTION

The invention relates to sampling of pressurized process fluids for on-stream and spot sampling of pressurized process fluid such as natural gas or the like having liquid entrained therein, or otherwise referenced as multiphase or "wet". The preferred embodiment of the present invention contemplates a cyclonic filtration apparatus integrated into a sample probe formed for insertion into a pressurized process fluid stream, the present system formed to separate and exclude entrained liquids in the process gas stream, preventing same from entering the sample stream.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long standing controversy between gas producers and gas transporters regarding entrained liquid typically present in most high BTU/cu ft. gas (rich or "wet" gas). Transporter tariffs require essentially liquid-free gas. Hydrocarbon liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

Therefore to fully comply with the current industry standards, there exists a compelling need to effectively prevent entrained liquids from entering sample systems. Membrane-tipped probes such as the A+ Corporation Genie Probe (see U.S. Pat. No. 6,357,304, U.S. Pat. No. 6,701,794, U.S. Pat. No. 6,904,816, U.S. Pat. No. 7,004,041, and U.S. Pat. No. 7,134,318) have been used for many years to shed entrained liquids inside pressurized pipelines. However, these systems can be overwhelmed with excessive liquid loading, causing the maximum allowable differential pressure to be exceeded, which tends to force liquids through the coalescing elements, and into the sample system.

The differential pressure needed to force liquids through the coalescing elements is a function of the surface tension of the liquid as well as the construction of the coalescing element. This can be further complicated by the use of various liquid chemicals, which are routinely injected into the process, gas such as corrosion inhibitors, amine and carbon dioxide inhibitors, as well as chemicals meant to dry the gas, like alcohols and glycols.

These liquid chemicals may have low surface tensions and may penetrate coalescing elements, in which case said liquid chemicals may combine with the sample, or lower the surface tension of entrained liquids at the coalescing membrane, making it easier for the said undesired liquids to penetrate and get past some coalescing elements. Also, some coalescing elements may have temperature limitations, and thus may be impractical for some applications.

Further, coalescing membranes or the like may have to be changed periodically as a maintenance precaution to insure reliable operation. Accordingly there is a need for a physical pre-filter to eliminate the bulk of the liquid entrained in the gas which would operate in a variety of conditions with little maintenance, and which is more reliable in operation than current systems.

Cyclonic separation techniques have been utilized in a variety of capacities for over 100 years. A typical cyclonic separator channels a fluid stream through a housing having a geometry formed to generate a vortex, exploiting centrifugal force with gravity and pressure differentials to separate liquid particles from gaseous streams, as well as other applications.

Cyclone-type pre-filters have been used for many decades. For example, D. W. Birnstingl describes a measuring head for a conductivity meter combining a conductivity cell with a cyclone filter to filter liquid in U.S. Pat. No. 3,471,775 filed in 1966.

UOP Inc. of Des Plains, Ill., describe a sampling probe that uses a V-shaped shield to pre-filter particles from sample (see U.S. Pat. No. 4,481,833 from 1984). Another company, Anarad Inc. of Santa Barbara, Calif., describes a filter probe for stack gas that uses an inertial filter with a constant bypass flow requirement to remove dust without clogging (U.S. Pat. No. 5,237,881 from 1993). The University of Akron describes a cyclone collection vessel combined with filter media for separation of a suspension (U.S. Pat. No. 6,210,575 from 2001). M & C Products Analysis Technology, Inc. of Ventura, Calif., describes an in situ particle separation system with filter media for separating particles from gas samples (U.S. Pat. No. 7,337,683 from 2008).

More recently, the General Electric Company of Schenectady, N.Y. describes sample probe for removing particles from a gas stream using a shield and a flow reversal technique (U.S. Pat. No. 8,087,308 from 2012). These devices are not used to remove entrained liquids from gas samples. No one in industry has contemplated using the cyclone technology to solve the problem of entrained liquids in natural gas samples.

Dekati Ltd of Finland offers the CYCLONE brand cyclonic separator for removal of large particles from a Sample Stream. This device is designed to be placed in a flue gas flow in a stack as well as exterior to the stack. In either instance, an isokinetic sampling probe is utilized to draw the sample. Various isokinetic nozzles are available and may be utilized interchangeably, depending upon the circumstances of use.

Other types of fluid separators may include:

Filter Vane Separators utilize a structure comprising a series of plates or baffles along a passageway to exploit inertial impaction of the fluids, combined with gravity, to facilitate separation.

Centrifugal separators which utilize centrifugal forces to separate the heavier fluid droplets or particles from the gas stream. Cyclone separators operate on this principal as well as well as knock-out drums.

Liquid/Gas coalescer cartridges, filters, membranes and the like are generally not suitable for removal of liquids in bulk, relying upon inertial impaction, the particles engaging a fibrous mass in a container which may include an indirect pathway utilizing inertial impaction and gravity to collect and drain fluid.

Mist Eliminators likewise rely upon the principal of inertial impaction, but instead of plates or baffles, relying upon fibers, meshes or the like.

A+ Corporation makes a self-cleaning filter under the trademark TORNADO (for example, model 602). It is an external cyclone type filter. Another external cyclonic filter is made by Collins Products Co, maker of the SWIRLKLEAN brand bypass filter which also uses a cyclone-type filter external to the pipeline, situated upstream the analyzer, although the SWIRLKLEAN system does not utilize gravity separation, instead exploiting a bypass technique as detailed at http://www.collins-products.com/.

To summarize, the prior art teaches various systems for removing liquid particulates or the like from a gaseous fluid stream. Removal of such entrained liquid is imperative as a component of gas analysis as detailed above, although such systems are imperfect and many designs can be overwhelmed by a liquid slug or the like. Anytime liquid is removed from the source and transported into the sample system, the liquid distorts the true composition of the sample.

However, due to shortcomings in the above systems there remains a long felt, but unresolved need for a system with the ability to reliably prevent liquids from overwhelming the separator to prevent liquid from entering the sample system, thus preventing sample distortion and contamination, which can equate to wrong analysis and very costly incorrect monetary exchanges. This is especially true at custody transfer points for both producers and transporters.

It would therefore be an improvement over the art to provide a system which does not require a bypass stream and with the required venting to the atmosphere or the ground, an undesirable requirement of several of the above referenced systems.

GENERAL SUMMARY DISCUSSION OF THE INVENTION

The present invention solves many of the shortcomings of prior art systems addressed supra. Unlike the known prior art systems, the present invention solves the problems discussed above. The device of the present invention is inserted into the pressurized pipeline to prevent liquids from entering the sample system. It does not require a bypass stream vented to the atmosphere, nor does it require any drain of liquids exterior to the pipeline which might otherwise occur onto the ground, or piped to a flare.

Rather, the present device prevents entrained liquids at the tip of the probe, thus ensuring that no liquids pass through to the sample probe and that a single gas-phase sample is taken. Further, the present invention also reduces or may even eliminate the need for filter elements that must be replaced or cleaned. It protects the entire sample system from contamination that otherwise would require costly downtime for cleaning or replacement. By preventing undesired liquids from entering the sample, the present lessens the likelihood of sample distortion and flawed analysis, especially when utilizing the current API and GPA sampling standards.

A first, preferred embodiment of the present invention, as illustrated in FIGS. 1-3, 8, 9, utilizes the cyclone filter mounted at the tip of a sample probe so as to be insert-able under pressure into the pressurized pipeline. This embodiment of the cyclone filter probe incorporates a coalescing element downstream the cyclone filter, so that the coalescing element coalesces entrained mist or very fine aerosol droplets which might otherwise pass through the cyclone, and thus prevents same from being introduced into the sample system. With this first embodiment, if a slug of liquid is present in the sample, the cyclone filter would act as a liquid block device, preventing most of said slug of liquid from passing therethrough, said coalescing element downstream said cyclone filter removing any remaining residual liquid from the sample stream.

A second embodiment utilizes the cyclone filter at the tip of a sample probe that is insert-able under pressure into pressurized pipelines like the first embodiment, but without any filter or coalescing element of any type behind the cyclone filter (FIGS. 4-6).

The inlet opening size, and length and diameter of the conical section, as well as the outlet and drain diameters of the probe tip may need to be properly proportioned to optimize the flow-to-filter ratio of the cyclone filter probe tip. This ratio must properly sized, taking into account the normal analytical flow rate in a gas or vapor only single phase sample so that the cyclone filter supplies the appropriate flow of sample. Further, the passageways must also be sized so that when liquid slugs are present, the cyclone filter can remove the liquid prior to entering the sample stream intended for the analyzer.

A third embodiment comprises a more permanent installation wherein a fixed probe is installed in a manner which would typically require a meter run section of pipeline or so to be depressurized for insertion and installation (FIG. 7). This third embodiment could have the other features of the first and second embodiments. The embodiments listed are not intended to be an exhaustive list of applications for the cyclone filter but only intended to show the need and some of the practical application of the invention.

The coalescing element downstream of the cyclone filter could be sintered plastic or metal or spun borosilicate glass or membrane material. A fourth embodiment would be various combinations of probe elements with the cyclone filter.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 11 is an end-of-pipe, partially cut-away view of an alternative embodiment of the invention of FIG. 1, wherein there is further provided a liquid block mechanism following (or downstream the cyclone filter, said liquid block mechanism at the tip of the probe or the like.

DETAILED DISCUSSION OF THE INVENTION

Figure 1:
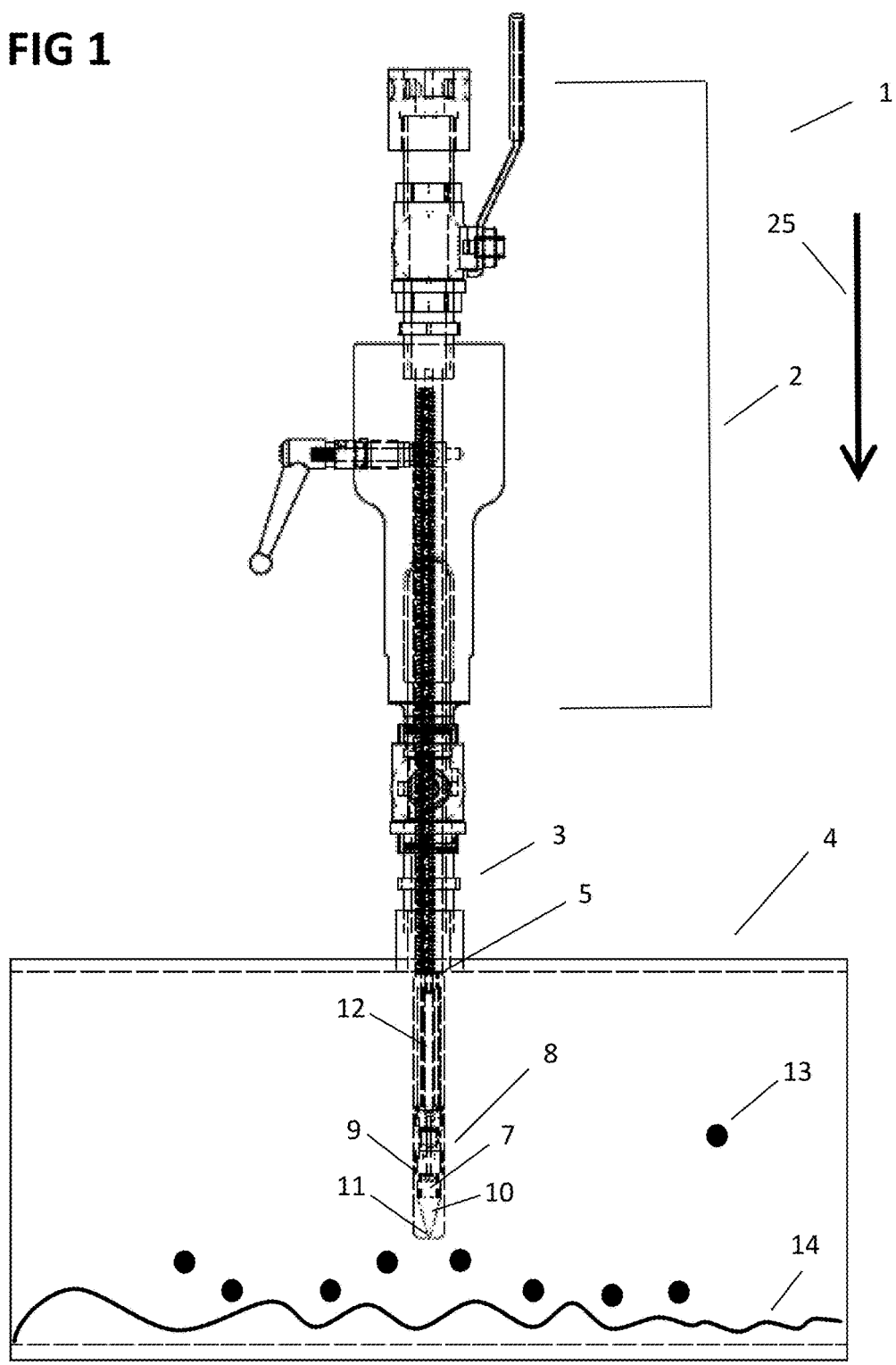
FIG. 1 is a frontal, partially cutaway view of the first embodiment of the present invention, illustrating a cyclone-type (also referenced as "cyclonic") filter device mounted to the tip of the sample probe, said probe inserted under pressure into a pressurized pipeline, the present embodiment further illustrating a coalescing element downstream of the cyclonic filter devices used as a liquid block.
Figure 2:
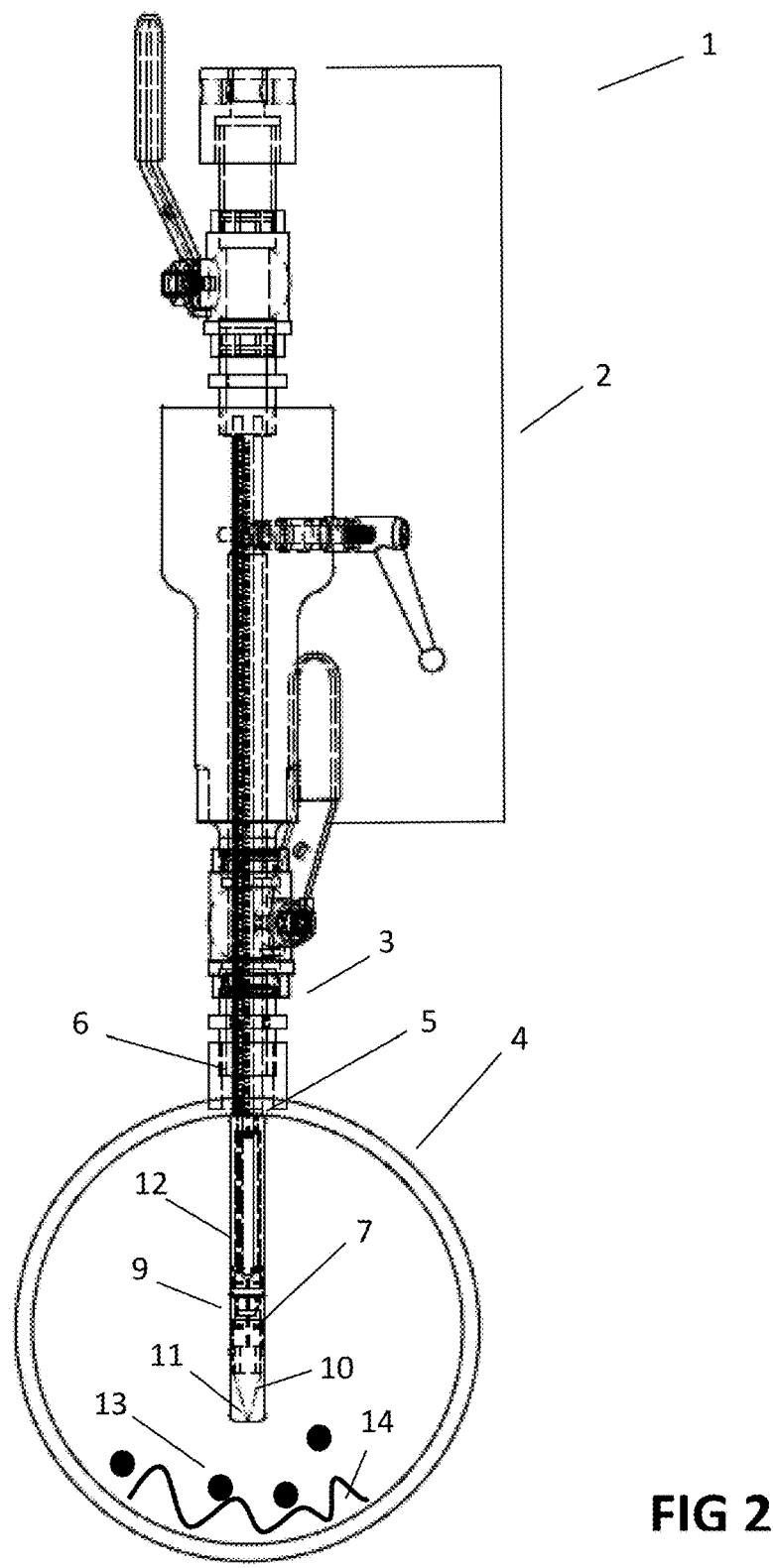
FIG. 2 is a side, end view through the pipeline, showing a partially cutaway view of the invention of FIG. 1.

The first embodiment 1 of the present invention (FIGS. 1-3, 8, 9) provides a cyclone separator or filter 8 with downstream coalescing filter or element 12 mounted to the tip 5 of a sample probe 2 or the like, said probe being insertable 25 under pressure into the pressurized pipeline 4 through a valve 3 or other available means. The cyclone filter probe of the first embodiment has a coalescing element 12 downstream the cyclone filter 8, so that the coalescing element 12 can capture, via coalescence, entrained mist or very fine aerosol droplets 13 that flow past the cyclone filter, so as to capture any remaining aerosol droplets beyond the cyclone filter, and preventing same from being introduced into the sample stream downstream the coalescing filter.

Accordingly, if a slug of liquid 14 is present in the sample stream entering the cyclone filter, said cyclone filter 8, in combination with the coalescing element 12, effectively diminishes or even fully prevents said large slug of liquid 14 (or any residual liquid therefrom) from entering via probe the sample passage 6 leading to the sample system.

Figure 6:
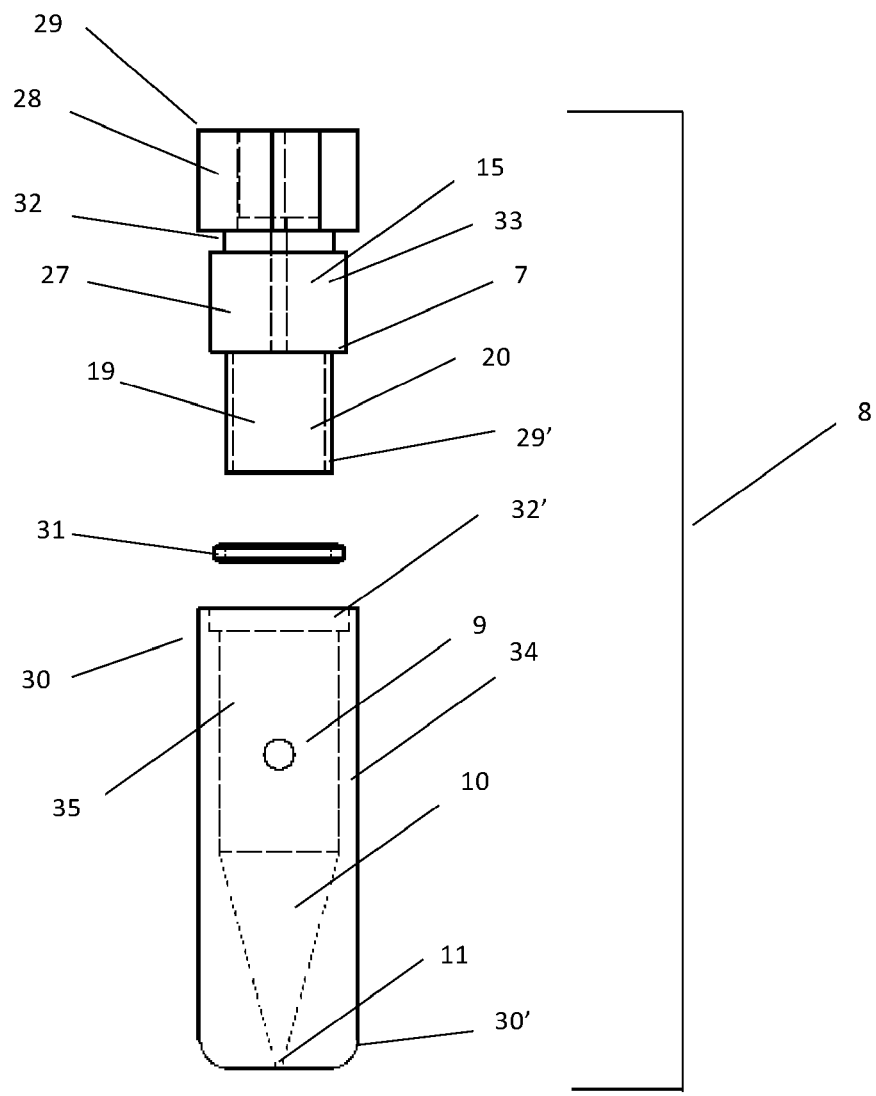
FIG. 6 is a side, close-up, partial, exploded view illustrating the various components of the cyclonic device as mounted to the probe tip, illustrating in phantom the internal structure of same.

As shown in FIG. 6, the cyclonic separator or filter 8 of the first embodiment of the present invention is formed of two sections, a mounting section 33 and a sleeve 34, said mounting section having a first end 29 formed to connect (for example, via connection 28 which may be threaded or other means) with, in the case of the first embodiment, coalescing element 12 (or, in the case of the second embodiment, the end 5 of the probe, as will be described further infra), and a second end 29' (of mounting section 33) formed to be inserted into the first end 30 of sleeve 34, into cylindrical cavity 35 formed therein, said second end 29' forming an insert 19 having a desired geometrical configuration as will be further disclosed below, the insert 19 in FIG. 6 shown as a cylinder (for exemplary purposes).

Situated between the insert 19 and the and the connection 28 section is a base 27 having an outer diameter 20 formed to engage inner diameter of cylindrical cavity 35 formed in sleeve 34 forming an internal barrier 7. An o-ring 31 or other seal is formed to sealingly engage groove 32 in mounting section 33 and groove 32' of sleeve 34. Also formed within sleeve 34, engaging the distal end of cylindrical cavity 35 is a conical cavity 10 having an inverted apex in the form of a drain 11 at the second end 30' of sleeve.

Figure 5:
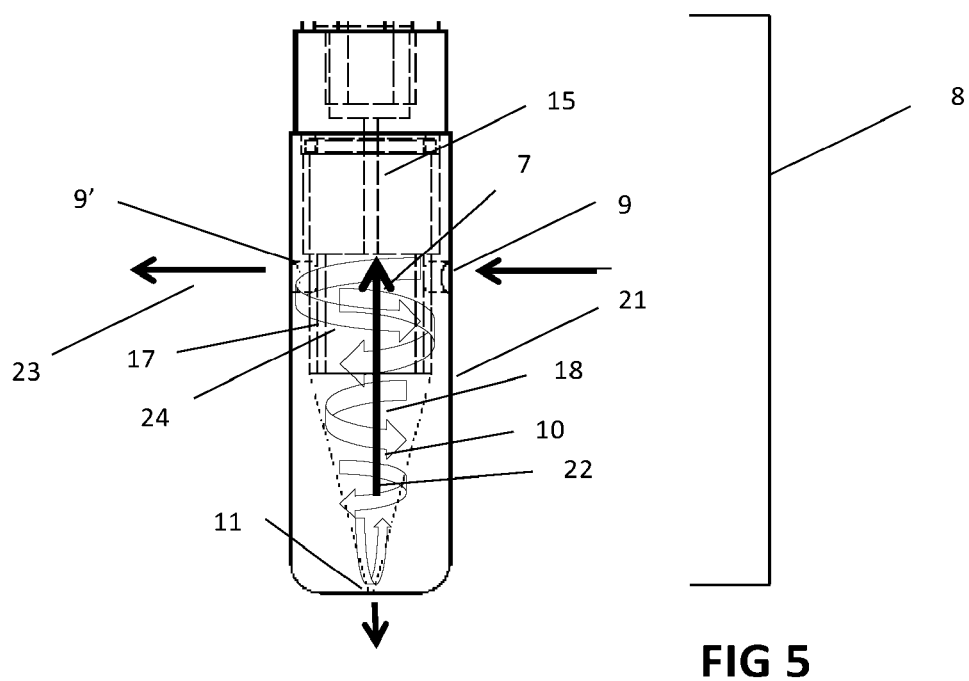
FIG. 5 is a side, partially cutaway view of the invention of FIG. 4, illustrating a close-up of the probe tip with cyclone apparatus forming the probe tip.

Continuing with FIGS. 5 and 6, the cyclone filter 8 is illustrated with an inlet 9 and outlet 9' formed through opposing sides of the cyclone filter 8 housing 21, the inlet 9 preferably facing the process flow so as to allow fluid flow tangentially therein and through a passage formed by the clearance 17 between internal barrier 7, shown in the form of a cylindrical insert 19, and inner walls of cylindrical cavity 35 formed in sleeve section 34, of housing 21.

A portion of the fluid flow exits 23 via the outlet 9' opposite inlet 9, the remaining flow spiraling down 24 the clearance 17 between internal barrier 7 and housing 21, down along the outer surface of internal barrier 7 to engage the lower inverted cone-shaped portion 10, which forms a cyclonic chamber to facilitate cyclonic action and fluid-liquid separation so that a gas or vapor only sample is drawn upward 18 through the lower pressure center of the vortex 22 to pass through fluid flow outlet 15, out of the cyclone filter/separator an, in the case of the first embodiment (FIGS. 1-3), into coalescing element 12 (again, where provided), where residual liquid particulates are coalesced and captured, providing a gaseous, liquid-free flow which flows through the probe passage to exit the probe to the analyzer downstream therefrom.

Any liquid particulates in the fluid stream are thereby cyclonically extracted from the stream and drain through drain port 11 at the base thereof, with any residual liquid taken out by coalescing element 12 downstream therefrom.

Figure 3:
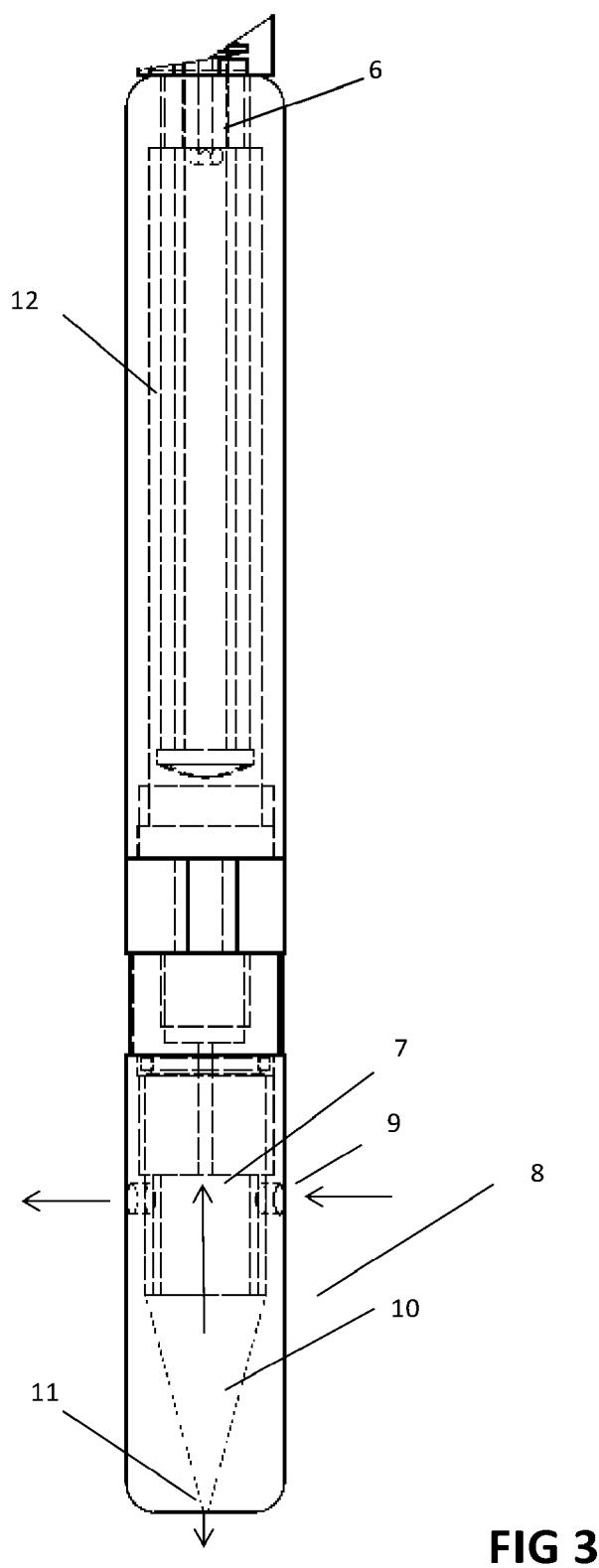
FIG. 3 is a side, cutaway view of the invention of FIG. 1, illustrating a close-up of the probe tip with cyclone apparatus, and downstream coalescing element.
Figure 10:
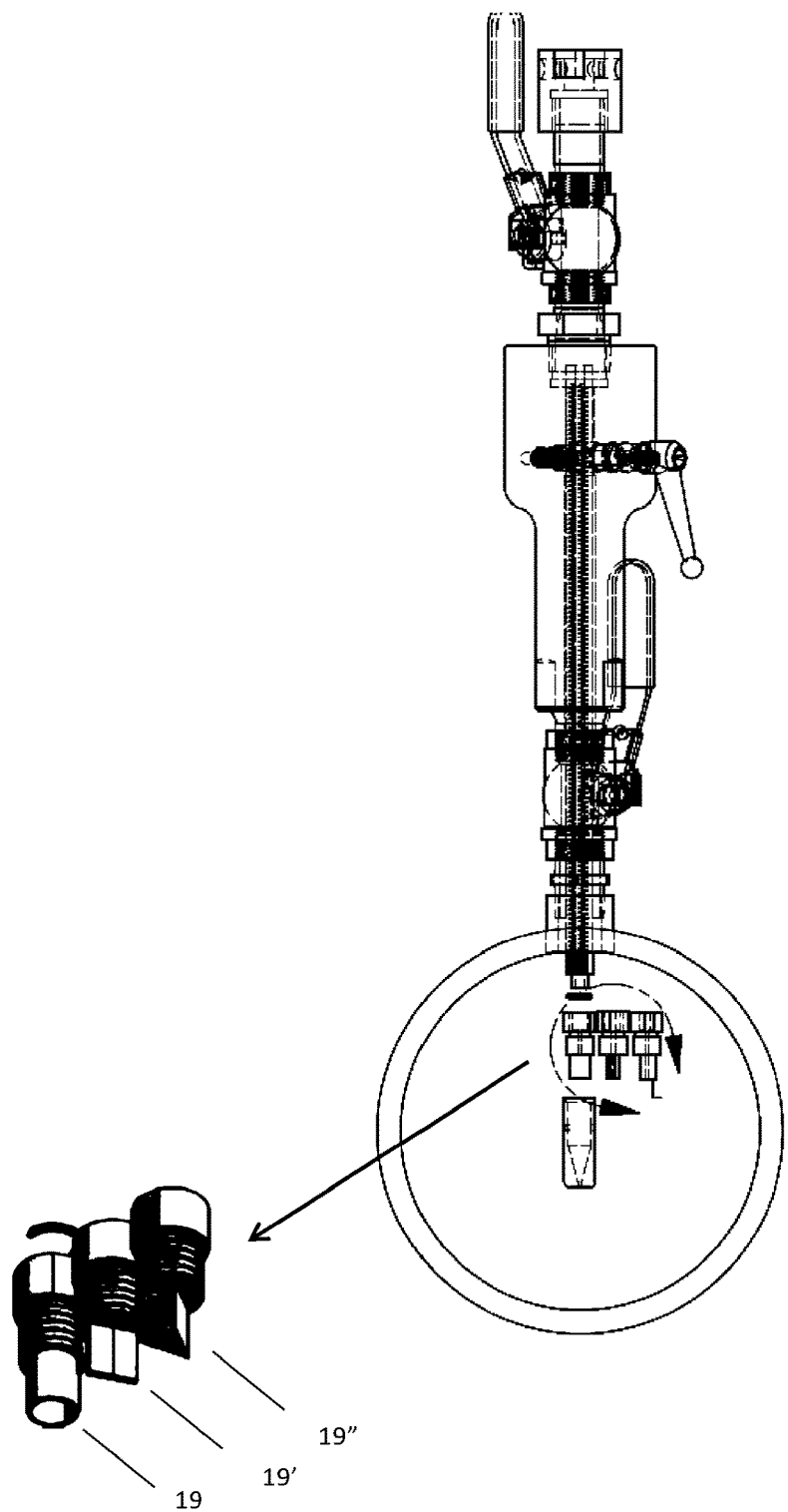
FIG. 10 is a side, partially cutaway view of the invention of FIG. 4, illustrating various alternative cyclone filter design profiles mountable to the probe tip forming the internal barrier to achieve the desired tangential flow, the optimal profile to be used depending upon the operational environment.

The illustration of the cylindrical insert 19 forming internal barrier 7 is not meant to limit the cyclone filter or separator design to have the cylindrical configuration as shown in FIG. 3, as other, different configuration geometries may be utilized depending upon the application and associated needs, including, for example, a linear or blade 19' configuration, and triangular or polygonal 19" configuration and others, as illustrated in FIG. 10, which may be interchangeably changed to selectively alter fluid flow patterns thereabout and therethrough, as the need arises. Further, threads can be provided about the outer diameter of the cylinder insert 19 to further enhance or facilitate the spiral effect as the fluid flows along same. In addition, the sizes and scales of the inserts may vary depending upon the application to vary the clearance between said insert and the outer housing, which forms the passage for the fluid stream flowing thereabout and therethrough.

The inlet opening size and the length and diameter of the conical section and internal barrier as well as the outlet and drain diameters of the probe tip may need to be sized for the flow to filter ratio of the cyclone filter probe tip. This ratio must be sized correctly so that under normal analytical flow rates in a gas or vapor only single phase sample, the cyclone filter supplies the appropriate flow of sample. Then the passageways must also be sized so that when liquid slugs are present, the cyclone filter can remove the liquid in sample intended for the analyzer. The material of construction of the coalescing element may be application dependent (i.e. may depend on process fluid, analytical flow rate thru probe, the properties of the type of liquid entrained, etc.). Further, the cyclonic chamber may be frustoconical, the inverted end having a drain passage formed therethrough.

Figure 4:
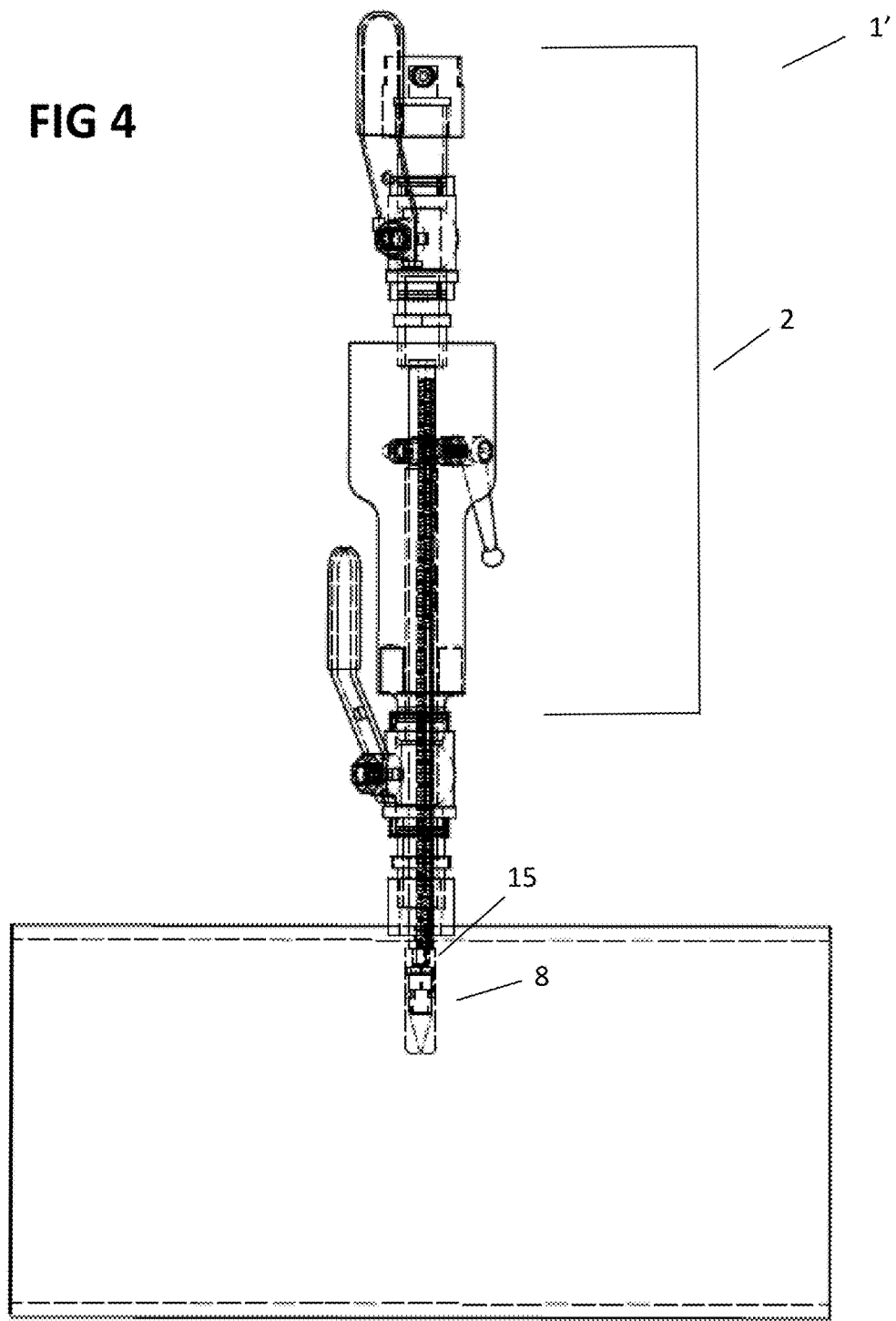
FIG. 4 illustrates a second embodiment of the present invention, comprising a frontal, partially cutaway view of the first embodiment of the present invention, illustrating a cyclone-type (also referenced as "cyclonic") filter device mounted to the tip of the sample probe, said probe inserted under pressure into a pressurized pipeline, the present embodiment without the coalescing element downstream of the cyclonic filter device utilized as a liquid block shown in the embodiment of FIG. 1.

A second embodiment would utilize a cyclone filter 8 at the tip of a sample or insertion probe 2 that is insertable under pressure into pressurized pipelines (FIGS. 5, 6), but without any filter or coalescing element of any type behind the cyclone filter (FIG. 4), a passage 15 downstream providing filtered gas therefrom.

Figure 7:
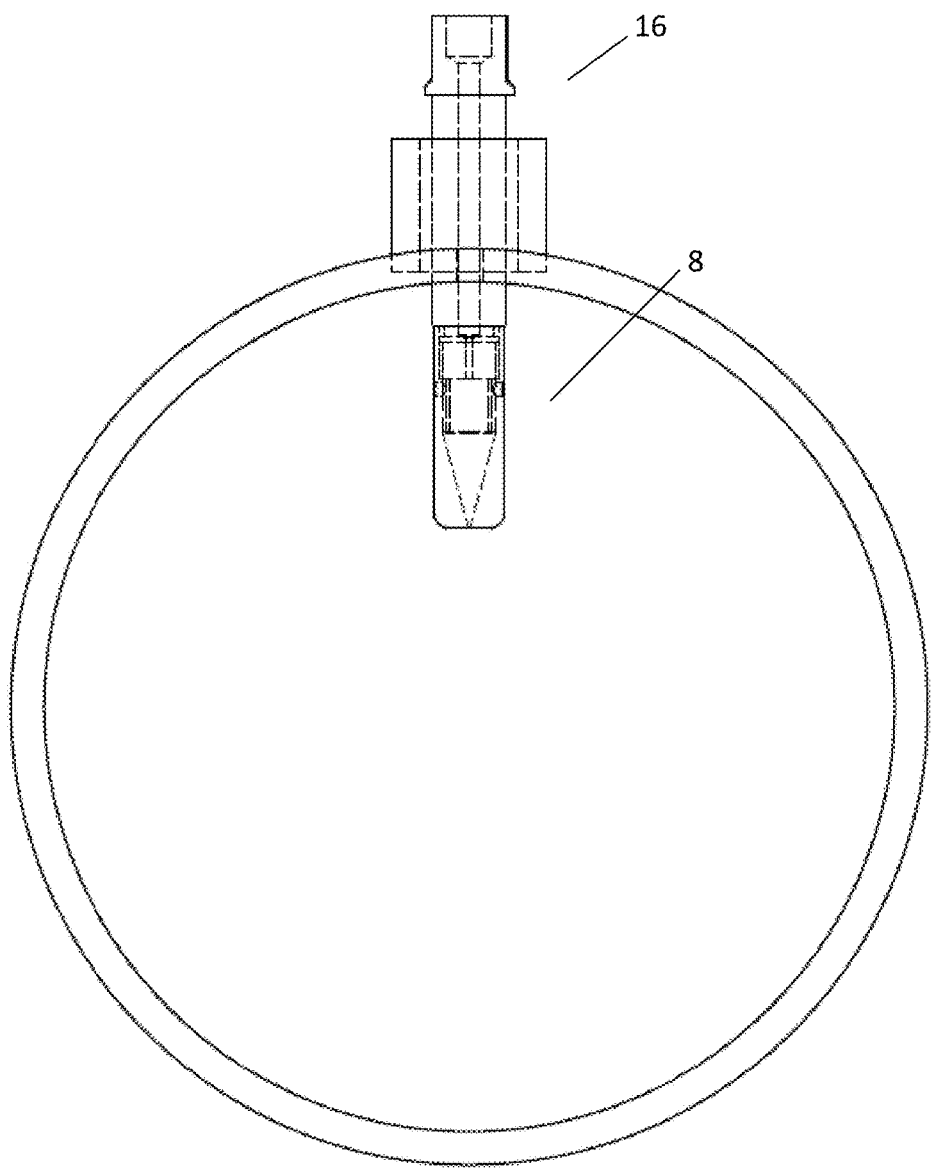
FIG. 7 is an partially cutaway view of a third embodiment of the present invention via the end of the pipe, illustrating wherein a fixed probe is utilized which would require a section of pipeline to be depressurized for insertion and installation of the probe, which could have the cyclone arrangement of the inventions of FIG. 1 or 4 mounted thereto.

A third embodiment 16 would be a fixed probe that requires a meter run section of pipeline to be depressurized for insertion and installation (FIG. 7). This third embodiment could have the other features of the first and second embodiments.

Figure 8:
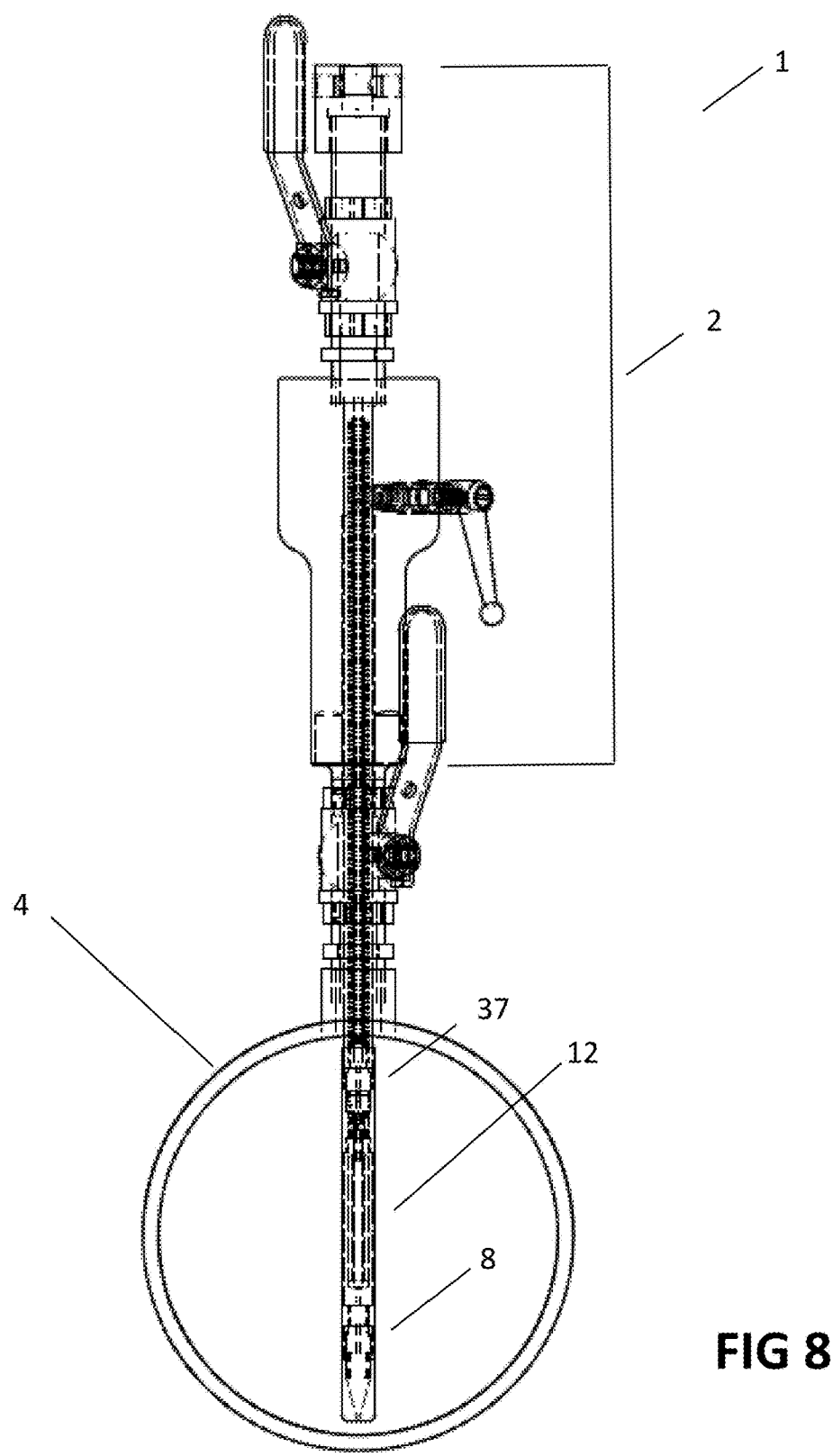
FIG. 8 is a fourth embodiment of the present invention, comprising an end of pipe, partially cut-away view of the invention of FIG. 1, but with the addition of a pressure reducing element (37) downstream the coalescing filter and cyclone apparatus at the probe tip.
Figure 9:
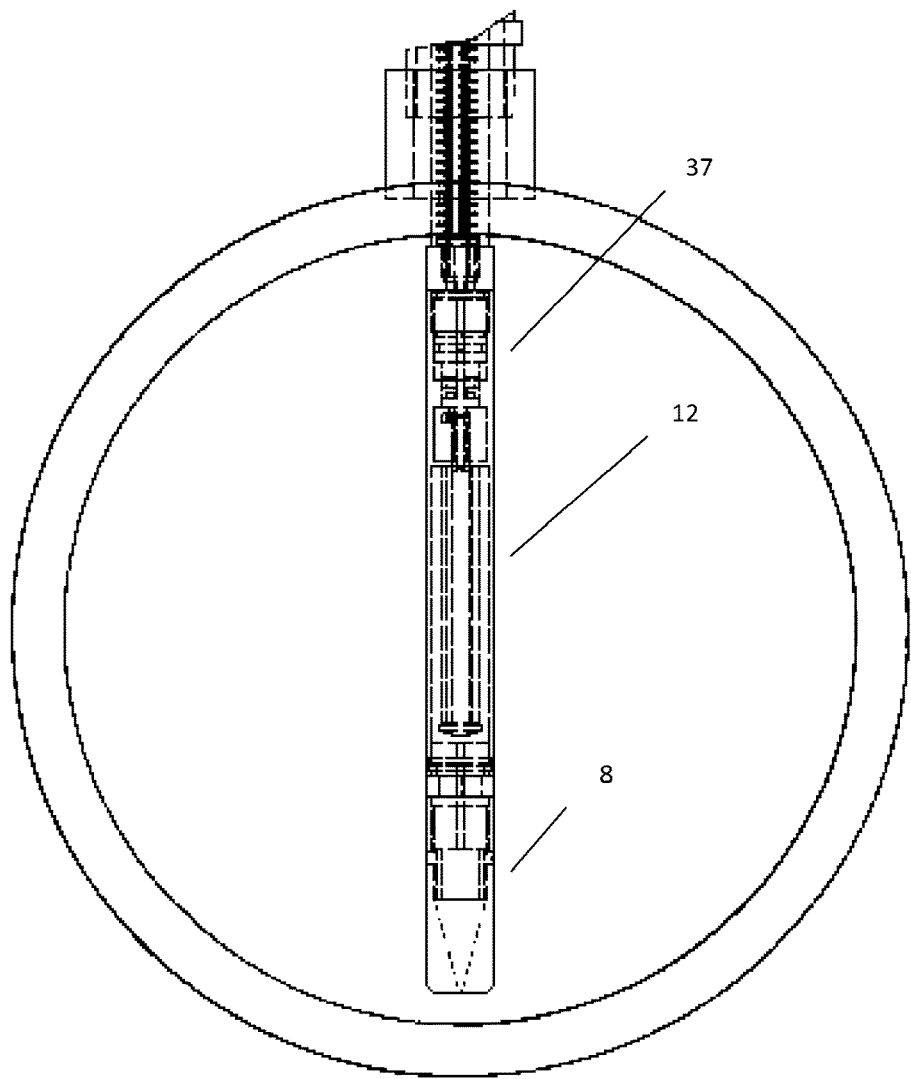
FIG. 9 is a partially cutaway, close-up view of the invention of FIG. 8 via the end of the pipe.
Figure 11:
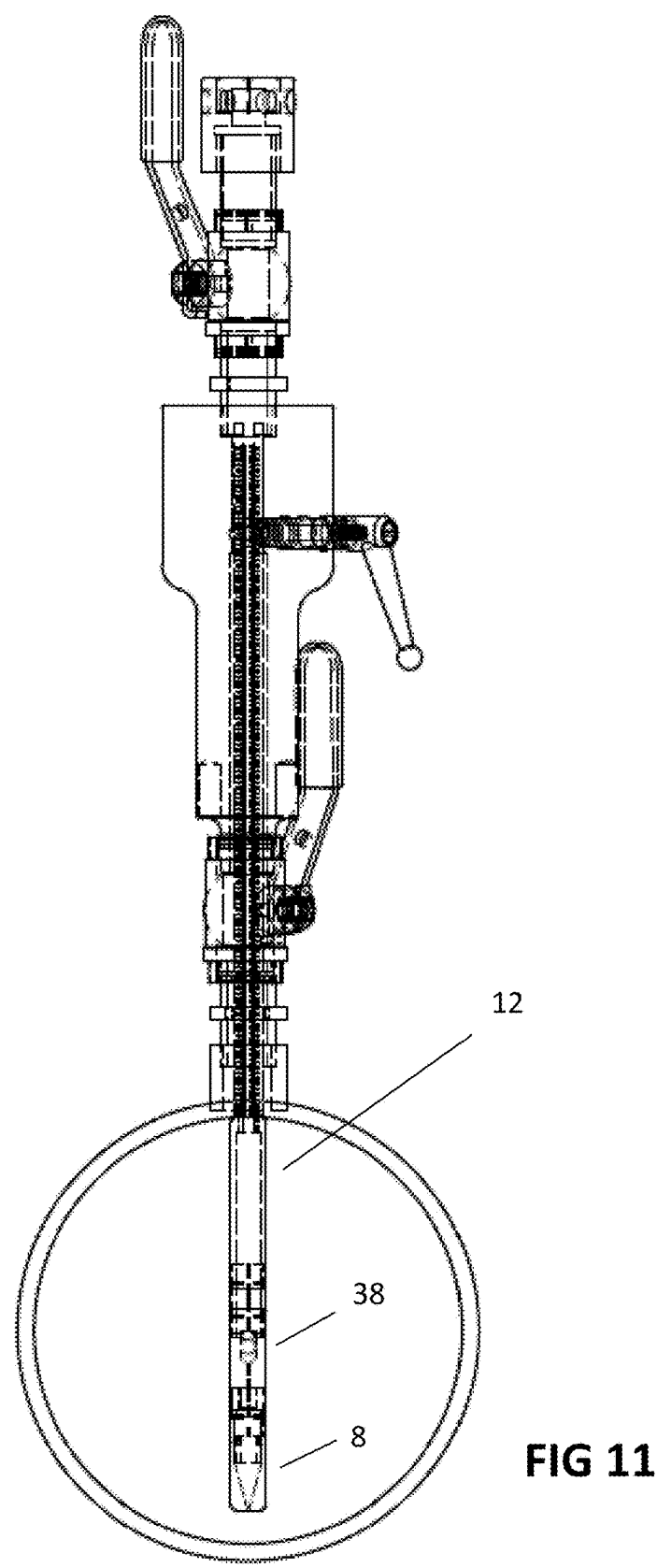
Figure 11A:
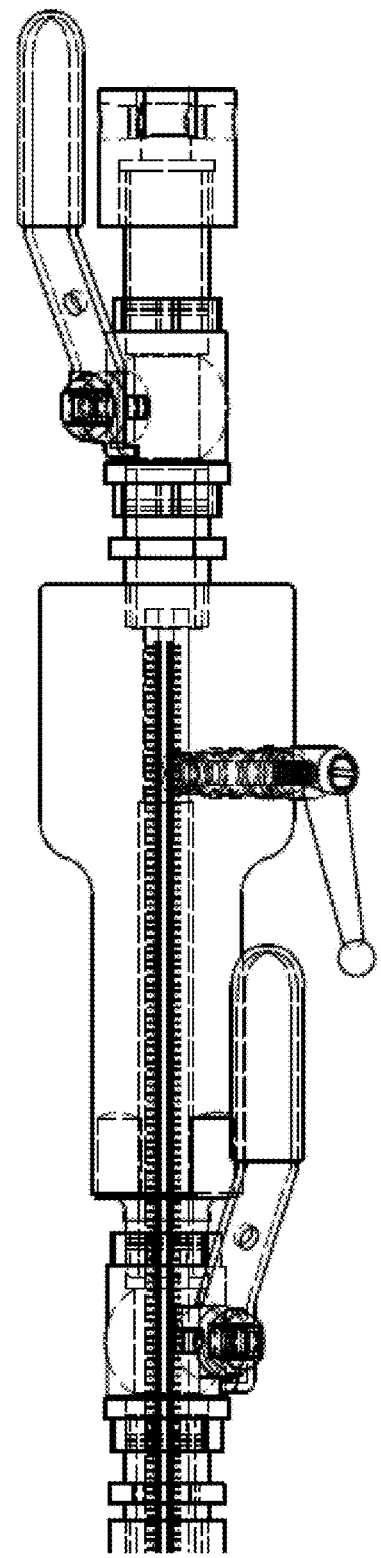
FIGS. 11A and 11B are close-up views of upper and lower portions, respectively, of FIG. 11.
Figure 11B:
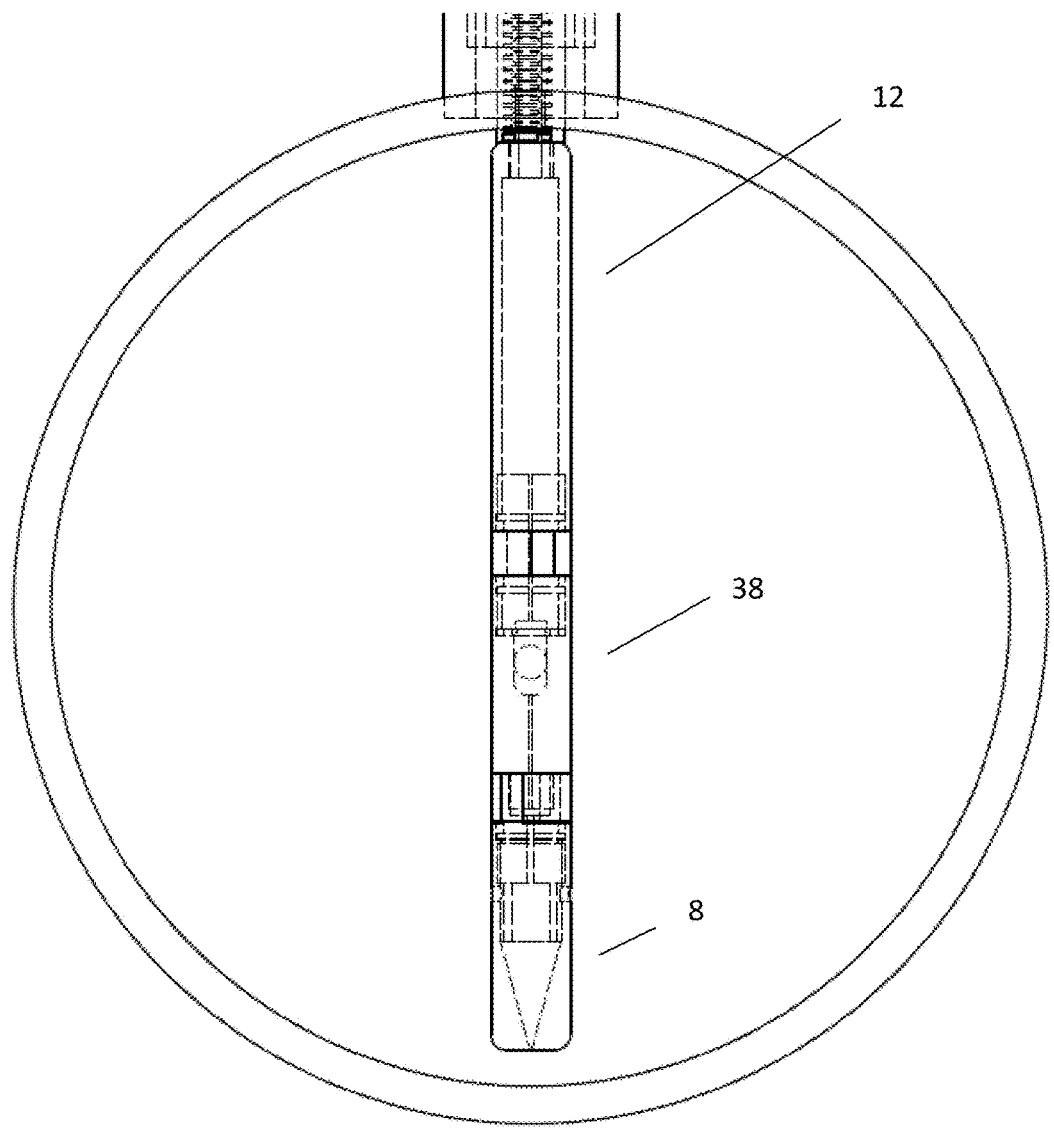

A fourth embodiment would be a combination of the cyclone filter 8 with the coalescing element 12, along with a pressure reducing device 37 downstream, shown in FIG. 8. Other combinations are envisioned such as the cyclone filter 8 with a liquid block 38 and a coalescing element 12 as seen in FIG. 11. The liquid block may comprise, for example, a float or other moveable body having a profile formed to engage a seal whereby, upon a mass of liquid flowing into said liquid block, said float or moveable body sealingly engages said seal, preventing the flow of said liquid mass therethrough. Other possible liquid block examples could include said a rotating ball engaging a wiper seal upon the liquid flowing into said liquid block, so as to block the flow of liquid therethrough, or an electronic mechanism in the form of a solenoid actuated door formed to prevent the flow of liquid through said liquid block, said actuated door actuated by a liquid sensor. Another example could be a flow enclosure having an inner wall, said flow enclosure having a geometry formed to resist the passage of liquid therethrough.

The embodiments listed are not intended to be an exhaustive list of applications for the cyclone filter but only intended to show the need and some of the practical applications of the invention.

ELEMENTS OF THE INVENTION

\# Description
1, 1' first, second embodiment of invention
2 insertion probe
3 valve
4 pipeline
5 tip
6 passage
7 internal barrier
8 cyclone filter
9, 9' inlet, outlet
10 conical portion
11 drain
12 coalescing element
13 liquid droplets
14 liquid slug
15 outlet passage
16 third embodiment of invention
17 clearance
18 upward
19,','' cylindrical, linear, triangular inserts
20 OD, outer wall
21 housing
22 vortex
23 exits
24 flow
25 insertable
26 flow
27 base
28 threaded end
29,' first, second ends
30,' first, second ends
31 O-ring
32,' groove
33 mounting section
34 sleeve section
35 cylindrical cavity
37 pressure reducer
38 liquid block The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device for sampling a fluid in a fluid stream, comprising:
   a first liquid block comprising a cyclonic separator mounted to a probe tip having an opening to receive incoming fluid from the fluid stream, said cyclonic separator having an internal geometry formed to facilitate cyclonic flow for the separation of liquid from said incoming fluid, and facilitate the passage of gas therethrough, said cyclonic separator further comprising:
   a mounting section having first and second ends, said first end formed to engage a probe, a second end forming an insert having a geometrical configuration, and therebetween a base having an outer diameter, and a seal situated between said base and said first end;
   a sleeve having first and second ends, said first end having a cylindrical cavity formed therein having an inner diameter formed to slidingly engage the outer diameter of said base and said seal, said cylindrical cavity formed to envelope said insert so as to provide a fluid passage therebetween, said insert having a first aperture to allow fluid flow from said fluid stream into said fluid passage and a second passage from said fluid passage to said fluid stream, and a conical portion associated with said second end of said sleeve for receiving fluid flow from said fluid passage;
   wherein a portion of fluid passing into said fluid passage from said first aperture is directed to said conical portion so as to facilitate cyclonic separation of liquid from gas, said sleeve formed to drain said liquid and flow said gas therefrom.

2. The device of claim 1, wherein said insert is exchangeable so as to change said geometrical configuration to selectively alter fluid flow patterns thereabout or therethrough.

3. The device of claim 1, wherein said insert is formed to be exchangeable to select an appropriate size and scale, depending on the application.

4. The device of claim 1, wherein said geometry of said cyclonic separator comprises a lower, conical chamber having a liquid drain formed therethrough.

5. The device of claim 4, wherein said device comprises an insertion probe.

6. The device of claim 5, wherein there is provided a coalescing element mounted to said probe downstream said cyclonic separator.

7. The device of claim 6, wherein there is provided a pressure reducer downstream said coalescing element.

8. The device of claim 5, wherein there is provided a second liquid block mounted to said probe downstream said cyclonic separator.

9. The device of claim 8, wherein said second liquid block comprises a moveable body having a profile formed to engage a seal whereby, upon a mass of liquid flowing into said liquid block, said moveable body sealingly engages said seal, preventing the flow of said liquid mass therethrough.

10. The device of claim 1, wherein said first liquid block is situated at the distal end of said probe and said probe comprises an insertion probe.

11. The device of claim 10, wherein said distal end forms an extension of said probe.

12. The device of claim 9, wherein said seal comprises gasket material.

13. The device of claim 9, wherein said seal comprises an o-ring.

14. The device of claim 9, wherein said moveable body of said second liquid block comprises a rotating ball, and said seal comprises a wiper seal, said rotating ball formed to engage said wiper seal upon the liquid flowing therein, so as to block the flow of liquid therethrough.

15. The device of claim 9, wherein said second liquid block comprises a solenoid actuated door formed to prevent the flow of liquid through said liquid block, said actuated door actuated by a liquid sensor.

16. The device according to claim 9, wherein said second liquid block comprises a flow enclosure having an inner wall, said flow enclosure having a geometry formed to resist the passage of liquid therethrough.

17. The device of claim 16, wherein said flow enclosure geometry comprises first and second barriers emanating from said inner wall.

18. The device of claim 17, wherein said first and second barriers comprises shelves.

19. The device of claim 18, wherein said probe is formed for insertion into said pipe via a process valve connection.

20. The device of claim 1, wherein said fluid stream is situated in a pipe having an inner wall and wherein said device comprises an insertion probe selectively insertable in said pipe so as to retrieve a sample of gas therefrom.

21. The device of claim 20, wherein said probe is formed for insertion into said pipe via a double block and bleed installation.

22. The device of claim 1, wherein said internal geometry of said cyclonic separator is in the form of an inverted frustoconical chamber having a drain formed therethrough.

23. The device of claim 2, wherein there is provided a coalescing element mounted to said probe downstream said cyclonic separator.

24. The device of claim 23, wherein there is provided a pressure reducer downstream said coalescing element.

25. The device of claim 24, wherein there is provided a second liquid block device mounted to said probe downstream said cyclonic separator.

26. A method of separating a gas from a gas/liquid flow, comprising the steps of:
   a. providing a cyclonic separator mounted to a probe tip having an opening to receive a fluid stream comprising gas having liquid therein from said gas/liquid flow, said cyclonic separator having an internal geometry formed to facilitate cyclonic flow, said cyclonic separator further comprising a mounting section having first and second ends, said first end formed to engage a probe, a second end forming an insert having a geometrical configuration, and therebetween a base having an outer diameter, and a seal situated between said base and said first end;
   a sleeve having first and second ends, said first end having a cylindrical cavity formed therein having an inner diameter formed to slidingly engage the outer diameter of said base and said seal, said cylindrical cavity formed to envelope said insert so as to provide a fluid passage therebetween, said insert having a first aperture to allow fluid flow from said fluid stream into said fluid passage and a second passage from said fluid passage to said fluid stream, and a conical portion associated with said second end of said sleeve for receiving fluid flow from said fluid passage;
   wherein a portion of fluid passing into said fluid passage from said first aperture is directed to said conical portion so as to facilitate cyclonic separation of liquid from gas, said sleeve formed to drain said liquid and flow said gas therefrom;
   b. flowing said fluid stream into said cyclonic separator,
   c. allowing said internal geometry of said cyclonic separator to facilitate formation of a cyclone therein;
   d. using said cyclone to facilitate separation of liquid from said fluid stream;
   e. draining said liquid, while facilitating the passage of gas therethrough.

27. The method of claim 26, wherein in step "b" said fluid stream comprises gas having entrained liquid.

28. The method of claim 27, wherein in step "a" there is further provided the step "a1" of providing a coalescing element downstream said cyclonic separator, and after step "e" there is provided the added step "f" of flowing said gas through said coalescing element, capturing said entrained liquid therein, and providing dry gas to the sample stream.

29. The method of claim 26, wherein in step "a" said insert is selected from a group of inserts depending on the application, each of said inserts having a different geometry so as to selectively alter fluid patterns thereabout or therethrough.

30. The method of claim 26, wherein in step "a" said insert is selected from a group of inserts, so as to provide appropriate size and scale depending on the application.

31. A method of sampling a process gas stream having entrained liquid therein, comprising the steps of:
   a. engaging a cyclonic separator to an insertion probe, said cyclonic separator further comprising a mounting section having first and second ends, said first end formed to engage a probe, a second end forming an insert having a geometrical configuration, and therebetween a base having an outer diameter, and a seal situated between said base and said first end;

a sleeve having first and second ends, said first end having a cylindrical cavity formed therein having an inner diameter formed to slidingly engage the outer diameter of said base and said seal, said cylindrical cavity formed to envelope said insert so as to provide a fluid passage therebetween, said insert having a first aperture to allow fluid flow from said fluid stream into said fluid passage and a second passage from said fluid passage to said fluid stream, and a conical portion associated with said second end of said sleeve for receiving fluid flow from said fluid passage;

wherein a portion of fluid passing into said fluid passage from said first aperture is directed to said conical portion so as to facilitate cyclonic separation of liquid from gas, said sleeve formed to drain said liquid and flow said gas therefrom;

b. inserting said insertion probe into the process gas stream having entrained liquid therein;

c. allowing a partial flow of a said process gas stream having entrained liquid therein to pass through said cyclonic separator, providing a sample flow;

d. diverting a portion of said sample flow to a cyclonic chamber in said cyclonic separator;

e. allowing said sample flow to interact with said cyclonic chamber to form a cyclone;

f. using said cyclone to separate liquid from said sample flow, providing a separated sample flow;

g. draining said liquid into said process gas stream.

32. The method of claim 31, wherein there is further provided added step "h" of flowing said separated sample flow through a liquid block.

33. The method of claim 32, wherein there is further provided added step "i" of flowing said separated sample flow through a coalescing element.

34. The method of claim 33, wherein there is further provided the added step "j" of flowing said separated sample flow through a pressure reducer, providing a reduced pressure, separated sample flow.

35. The method of claim 33, wherein there is further provided the added step "k" of flowing said reduced pressure, separated sample flow to an analyzer.

36. The method of claim 31, wherein in step "a" said insert is selected from a group of inserts depending on the application, each of said inserts having a different geometry so as to selectively alter fluid patterns thereabout or therethrough.

37. The method of claim 31, wherein in step "a" said insert is selected from a group of inserts, so as to provide an appropriate size and scale depending on the application.

38. A modular cyclonic separator, comprising:

a mounting section having first and second ends, said first end formed to engage a probe, a second end forming an insert having a geometrical configuration, and therebetween a base having an outer diameter, and a seal situated between said base and said first end;

a sleeve having first and second ends, said first end having a cavity formed therein having an inner diameter formed to slidingly engage the outer diameter of said base and said seal, said cavity formed to envelope said insert so as to provide a fluid passage therebetween, said insert having a first aperture to allow fluid flow from said fluid stream into said fluid passage and a second passage from said fluid passage to said fluid stream, and a conical portion associated with said second end of said sleeve for forming a cyclone chamber formed to receive fluid flow from said fluid passage;

wherein a portion of fluid passing into said fluid passage from said first aperture is directed to said conical portion so as to facilitate cyclonic separation of liquid from gas, said sleeve formed to drain said liquid and flow said gas therefrom; and wherein said insert is formed to be exchangeable to provide an appropriate size and scale depending on the application.

39. The device of claim 38, wherein said insert is exchangeable so as to change said geometrical configuration to selectively alter fluid flow patterns thereabout or therethrough.

\* \* \* \* \*